United States Patent [19]

Michelson et al.

[11] Patent Number: 5,246,832
[45] Date of Patent: Sep. 21, 1993

[54] PLATELET ANALYSIS IN WHOLE BLOOD

[75] Inventors: Alan D. Michelson, Boylston; Anita S. Kestin, Wellesley, both of Mass.

[73] Assignee: University of Massachusetts Medical Center, Worcester, Mass.

[21] Appl. No.: 540,840

[22] Filed: Jun. 20, 1990

[51] Int. Cl.$^5$ .................. C12Q 1/00; G01N 33/53; G01N 33/567; G01N 33/554; A01N 1/02; A61K 35/14; C07K 3/00; C07K 13/00

[52] U.S. Cl. .......................... 435/7.2; 435/2; 435/7.1; 435/7.21; 435/7.8; 435/960; 435/973; 436/503; 436/579; 530/388.22; 530/388.25

[58] Field of Search ............... 435/2, 7.2, 7.24, 960, 435/2, 7.1, 7.21, 7.8, 973; 436/503, 519; 530/388.22, 388.25

[56] References Cited

PUBLICATIONS

Michelson et al (1987) Thrombin Induced Charges . . . Blood 70: 1673–1678.
Sanford et al (1987) Detection of Actuated . . . Blood 70: 307–315.
Adelman et al (1988) Abstract Blood 72(5) 1530–1535.
Ault et al (1989) Correlated Measurement . . . Cytometry 10: 448–455.
Adelman et al (1985) Abstract Blood 66(2) 423–7.
Michelson (1987) Flow Cytometric Analysis . . . J Lab Clin Med 110: 346–354.
Yamamoto et al (1991) Abstract Blood 77(8) 1740–1748.
Sims et al (1991) Abstract J Biol Chem 266(12) 7345–52.
Sanford et al (Jan. 1989) Epinepherin Induces . . . Blood 73: 150–158.
Nomura et al (Aug. 1989) Abstract Nippon Katsueki Gakkai Zasshi 52(5) 895.
Lengrae et al (Apr. 1989) Studies on the Mechanism . . . Blood 73: 1226–1234.
Michelson et al (1991) Abstract Blood 77(4) 770–779.
Charles S. Abrams, et al., "Direct Detection of Activated Platelets and Platelet-Derived Microparticles in Humans", *Blood*, vol. 75, No. 1 (Jan. 1) 1990; 128–138.
Miraglia et al., "Measurement of Blood Coagulation Factor XIIIa Formation in Plasma Containing Glycyl-L-prolyl-L-arginyl-L-proline", 144:165, 1985.
Johnston et al., "Heterogeneity of Platelet Secretion in Response to Thrombin Demonstrate by Fluorescence Flow Cytometry", Blood 69:1401, 1987.
George et al., "Platelet Surface Glycoproteins", J. Clin. Invest. 78:340, 1986.
Michelson et al., "Thrombin-Induced Changes in Platelet Membrane Glycoproteins Ib, IX, and IIb-IIIa Complex", Blood 70:5 (1987) pp. 1673–1678.
Shattil et al., "Detection of Activated Platelets in Whole Blood Using Activation-Dependent Monoclonal Antibodies and Flow cytometry", Blood 70:307 (1987).
Vickers et al., "Phosphatidylinositol 4,5-bisphosphate is selectively retained by platelet-fibrin clots Formed by Thrombin", Biochem, J. 245:649 (1987).
Harfenist et al., "The use of the synthetic Peptide, gly-Pro-Arg-Pro, in the Preparation of Thrombin-degranulated Rabbit Platelets", Blood 59–952 (1982).
Ault et al., "Correlated Measurement of Platelet Release and Aggregation in Whole Blood", Cytometry 10:448 (1989).
Frishman et al., "Reversal of Abnormal Platelet Aggregability and Change in Exercise Tolerance in Patients with Angina Pectoris Following Oral Propranolol", Circulation 50:887 (1974).
Sagel et al., "Increased Platelet Aggregation in Early Diabetus Mellitus", Annals of Internal Medicine 82:733 (1975).

(List continued on next page.)

Primary Examiner—Christine M. Nucker
Assistant Examiner—D. P. Preston
Attorney, Agent, or Firm—Fish & Richardson

[57] ABSTRACT

Method of determining, in a blood sample, containing unwashed platelets and fibrinogen, the state of thrombin reactivity of the platelets by adding thrombin to the sample in the presence of an agent for inhibiting fibrin polymerization, and then detecting activated platelets.

18 Claims, 4 Drawing Sheets

PUBLICATIONS

Carbalho et al., "Platelet Function in Hyperlioproteinemia", New Eng. J. of Med. 290:434 (1974).

Hawkins, "Smoking, Platelets and Thrombosis", Nature 236:450 (1972).

Levine et al., "Platelet Activation and Secretion Associated with Emotional Stress", Circulation 71:1129 (1985).

LeGrand et al., "Studies on the Mechanism of Expression of Secreted Fibrinogen on the surface of activated Human Platelets", Blood 73:1226-1234 (1989).

Kaplan et al., "Effect of Fibrin on Endothelial Cell Production of Prostacyclin and Tissue Plasminogen Activator", Arterioschlerosis 9:43 (1989).

Hantgan, "Fibrin protofibril and fibrinogen binding to ADP-stimulated platelets: evidence for a common Mechanism", Biochemica et Biophysics Acta 968:24 (1988).

Jen et al., "Direct platelet-fibrin interaction that does not require platelet activation", Am. J. Physiology 253:H745 (1987).

Achyuthan et al., "Gly-Pro-Arg-Pro modifies the glutamine residues in the α and γ-chains of fibrinogen; Inhibition of Transglutaminas cross-Linking", Biochimica et Biophysica Acta 872:261 (1986).

Harfenist et al., "Comparison of the Interactions of Fibrinogen and Soluble Fibrin with Washed Rabbit Platelets Stimulated with ADP", Thrombosis and Haemostatis, p. 183 (1985).

Hantgen et al., "Platelets Interact with Fibrin only after Activation", Blood 65:1299 (1985).

Tuszynski et al., "Association of Fibrin with the Platelet Cytoskeleton", J. Biol. Chem. 259:5247 (1984).

Henrikson et al., "Evidence That Activation of Platelets and Endothelium by Thrombin Involves Distinct Sites of Interaction", J. Biol. Chem. 258:13717 (1983).

Plow et al., "Inhibition of fibrinogen binding to human platelets by the tetrapeptide glycyl-L-prolyl-L-arginyl-L-proline", Proc. Nat. Aca. Sci. 79:3711 (1982).

Vickers et al., "Platelet-Fibrin Clots Formed by Thrombin selectively retain phosphatidylinositol 4,5--bisphosphate (Pip2)", Thrombosis and Haemostasis 58(1):279, Abstract No. 1010 (1987).

Laudano et al., "Synthetic peptide derivatives that bind to fibrinogen and prevent the polymerization of fibrin monomers", Proc. Nat. Aca. Sci. 75:3085 (1978).

Laudano et al., "Studies on synthetic Peptides That bind to Fibrinogen and Prevent Fibrin Polymerization Structural Requirements, Number of Binding sites, and Species Differences", Biochem. 19:101 (1980).

Laudano et al., "Influence of Calcium Ion on the binding of Fibrin Amino Terminal Peptides to Fibrinogen", Science 212:457 (1981).

Berndt et al., "Thrombin Interactions with Platelet Membrane Proteins", Annals NY Aca. Sci.

PLATELET ANALYSIS IN WHOLE BLOOD

Funding for this invention was provided by a grant from the National Institute of Health, and the Federal Government has certain rights in the invention.

BACKGROUND OF THE INVENTION

This invention relates to, e.g., determining the activation potential of blood platelets and, specifically, the reactivity of platelets to α-thrombin.

Upon becoming activated, human blood platelets undergo changes in platelet surface membrane receptors, which may result in platelet aggregation, interaction with fibrin fibers, and the resulting formation of a thrombus. In certain disease states, e.g., coronary artery disease and diabetes, platelets may exist in a hyperreactive state, resulting in increased risk to the patient of thrombosis. Early detection of platelet hyperreactivity can permit the timely administration of antiplatelet drugs.

α-thrombin is considered the most physiologically important activator of platelets. Quantitative determination of thrombin-induced changes in specific receptors, as measured by monoclonal antibody binding, has been carried out in assays performed on washed and resuspended platelets. Activation of platelets by adenosine diphosphate and epinephrine has been measured in a whole blood assay by flow cytometry.

It is known that the tetrapeptide glycyl-L-prolyl-L-arginyl-L-proline (GPRP), an analog of the amino terminus of the α-chain of fibrinogen and the fibrin monomer, binds to fibrinogen and, under some experimental conditions, inhibits fibrin polymerization.

SUMMARY OF THE INVENTION

In general, the invention features a method of determining, in a blood sample containing unwashed platelets and fibrinogen, the state of thrombin reactivity of the platelets by adding thrombin to the sample in the presence of an agent which inhibits fibrin polymerization, and then detecting activated platelets in the sample as an indication of thrombin reactivity.

Preferably, the agent which inhibits fibrin polymerization is one which does so by competitive inhibition. A particular class of such molecules are those capable of binding to fibrinogen and fibrin monomer to inhibit fibrin[ogen]-fibrin[ogen] interactions which otherwise would lead to clot formation. Such inhibitory agents include molecules which mimic, in their fibrinogen binding property, the action of the amino terminal half of native human fibrinogen. Particular such agents are peptides, preferably those containing between two and twenty amino acid residues, and more preferably peptides containing between four and ten amino acid residues. It is preferred that the peptide have at least 75% homology with a region contained in the amino terminal half of native human fibrinogen. The currently most preferred inhibitory peptide is the tetrapeptide glycyl-L-prolyl-L-arginyl-L-proline. Another suitable agent is an antibody capable of binding to the amino terminal half of native human fibrinogen.

In preferred embodiments, prior to detecting activated platelets, all platelets are identified using an antibody directed against a platelet surface antigen other than GPIb; this permits the measurement of changes in the clinically important antigen GPIb upon activation; platelet surface GPIb decreases on α-thrombin activation. A suitable antigen for the identification of all platelets is GPIV, which is, in the peripheral blood, limited to platelets and monocytes; the latter can be simply gated out on the basis of size (light scatter).

The whole blood assay for the detection of platelet response to the activating agent thrombin, in the presence of an agent that inhibits the polymerization of fibrin monomers (and thus fibrin clot formation) and fibrinogen binding to platelets (and thus platelet aggregation) permits sensitive determination of the reactive state of a patient's platelets on samples as small as a few microliters. Thus, the assay is suitable for routine clinical use where a rapid assay that can minimize the amount of patient blood drawn is needed for the assessment of patient risk from abnormal platelet reactivity.

In another aspect, the invention features a method of measuring the total platelet-to-GPIb ratio in a platelet-containing sample by identifying total platelets using a platelet surface antigen other than GPIb, and measuring GPIb; the other platelet surface antigen is preferably GPIV, and the sample is preferably a whole blood sample which contains monocytes which are gated out by size. As will be described below in more detail, the method is particularly useful when used in conjunction with bleeding time tests.

Other features and advantages of the invention will be apparent from the following description of the preferred embodiment thereof, and from the claims.

BRIEF DESCRIPTION OF THE DRAWINGS

The present invention will be better understood by reference to the Description of the Preferred Embodiments when taken together with the attached drawing, wherein: incubated sequentially at 22° C. with or without 10 U/ml α-thrombin (15 mins), with phycoerythrin-streptavidin (15 mins), and with an equal volume of 2% formaldehyde (30 mins). The left panels display the light scattering properties of all OKM5-FITC-positive cells. Platelets were identified by their OKM5-positivity (green fluorescence) and their characteristic light scatter (box 1). Box 2 contains monocytes and any platelet-to-platelet or platelet-to-monocyte aggregates. The binding of the activation-dependent monoclonal antibody S12 (right panels) was determined from the phycoerythrin (red) fluorescence of the OKM5-positive particles in box 1.

DESCRIPTION OF THE PREFERRED EMBODIMENTS

Assay Steps

Figure 1:
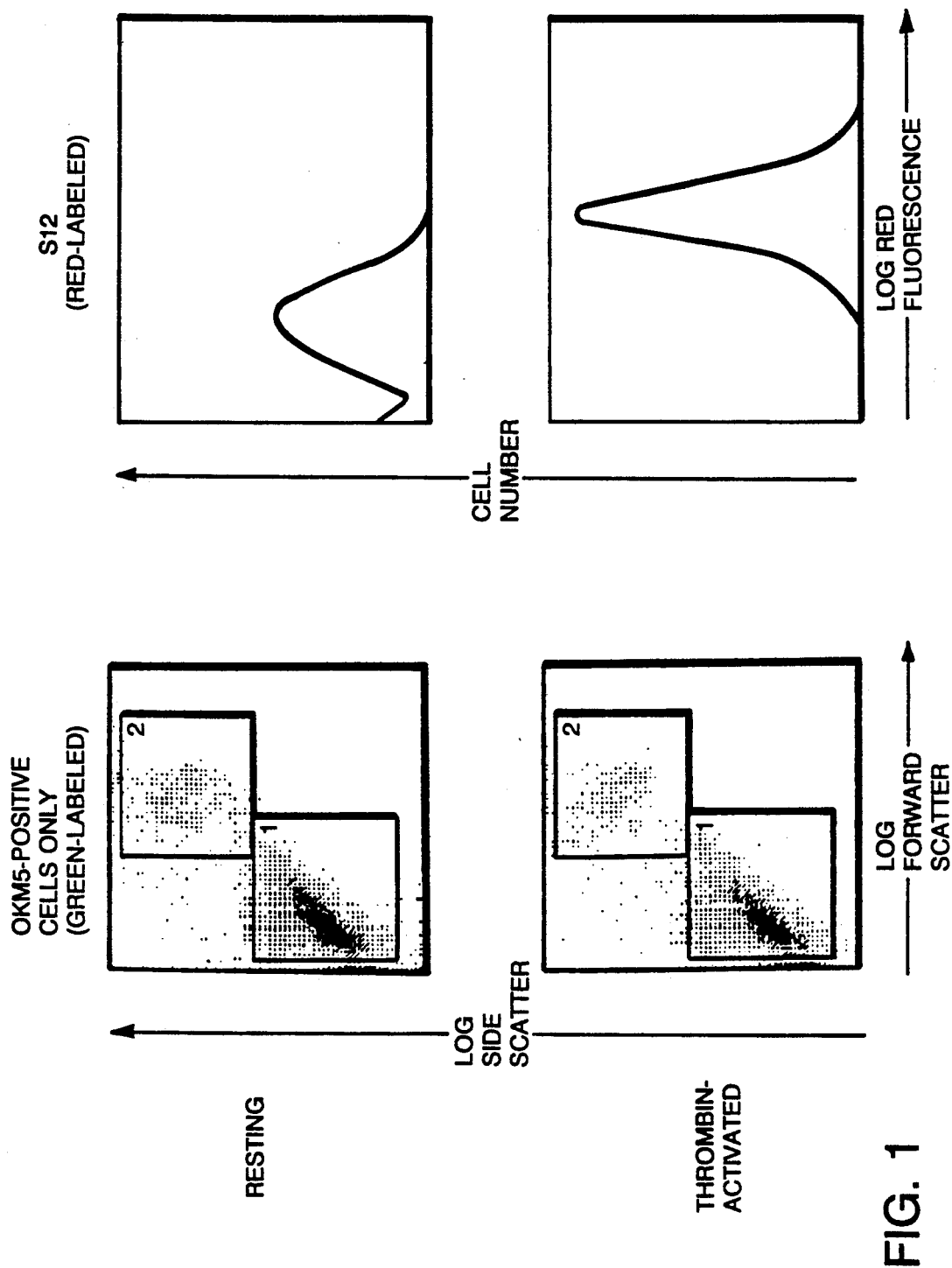

The detection of thrombin-induced platelet activation (platelet reactivity) in a whole blood assay according to the invention involves inhibition of platelet aggregation and fibrin clotting using a peptide such as the tetrapeptide glycyl-L-prolyl-L-arginyl-L-proline (GPRP). The extent of thrombin-induced platelet activation is measured by standard techniques, most conveniently by flow cytometry. To a sample of blood from a patient whose platelet reactivity state is to be determined is added GPRP, $\alpha$-thrombin to induce platelet activation, and a monoclonal antibody specifically reactive with activated platelets. The amount of monoclonal antibody binding to individual platelets is detected by flow cytometry, and the result is correlated with results from a standard reaction to determine the state of hypo- or hyperreactivity of the patient's platelets. The specific details of the assay procedure are given in the example below.

EXAMPLE

Monoclonal Antibodies Used

Eight murine monoclonal antibodies used or usable in this Example are listed in the Table below.

| Antibody | Platelet Surface Antigen |
|---|---|
| 6D1 | GPIb (von Willebrand factor receptor) |
| FMC25 | GPIX |
| AK1 | GPIb-IX complex |
| AK3 | GPIb (macroglycopeptide portion of $\alpha$ chain) |
| PAC1 | GPIIb-IIIa complex (fibrinogen receptor) |
| 10E5 | GPIIb-IIIa complex (fibrinogen receptor) |
| OKM5 | GPIV (thrombospondin receptor) |
| S12 | GMP-140 |

6D1 (provided by Dr. Barry S. Coller, SUNY, Stony Brook, N.Y.) is directed against the von Willebrand factor receptor on the glycocalicin portion of the $\alpha$-chain of platelet membrane GPIb. FMC25 (provided by Dr. Michael C. Berndt, University of Sydney, Australia) is directed against platelet membrane GPIX. AK1 (provided by Dr. Berndt) is directed against the platelet membrane GPIb-IX complex. AK1 only binds to the intact GPIb-IX complex, not to uncomplexed GPIb or GPIX. AK3 (provided by Dr Berndt) is directed against the macro-glycopeptide portion of the $\alpha$ chain of platelet membrane GPIb. PAC1 (provided by Dr. Sanford J. Shattil, University of Pennsylvania, Philadelphia) is directed against the fibrinogen receptor on the platelet membrane GIIb-IIIa complex. 10E5 (provided by Dr. Coller) is also directed at, or very near, the fibrinogen receptor on the platelet membrane GPIIb-IIIa complex. Unlike PAC1, 10E5 binds to resting platelets. OKM5 (Ortho Diagnostic Systems Inc., Raritan, N.J.) is directed against the thrombospondin receptor on platelet membrane GPIV. S12 (provided by Dr. Rodger P. McEver, University of Oklahoma) is directed against GMP-140. GMP140, also referred to as platelet activation-dependent granule-external membrane (PADGEM) protein, is a component of the alpha granule membrane of resting platelets that is only expressed on the platelet plasma membrane after platelet activation and secretion. All the antibodies listed are of the IgG class except PAC1, which is IgM.

The identification of platelets by a surface antigen other than GPIb (such as GPIV) allows measurement of changes in GPIb brought about by platelet activation. The assay of the invention identifies all platelets (whether activated or not) using an anti-platelet antibody labeled with a first fluorophore emitting at a given wavelength, and then identifies the $\alpha$-thrombin-activated subset using a second, activated platelet-specific antibody labeled with a second fluorophore emitting at a second, different wavelength.

Blood Sample Preparation

Blood was drawn by venipuncture from healthy adult volunteers who were not cigarette smokers and who had not ingested aspirin within the previous ten days. In order to avoid an increase in platelet activatibility between 6 a.m. and 9 a.m., blood samples were not drawn between these hours. The blood was drawn directly into a plastic syringe containing 1/7 volume of acid-citrate-dextrose (85 mM trisodium citrate, 71 mM citric acid, 111 mM dextrose, pH 4.5), resulting in a final pH of 6.5. To minimize platelet activation during blood drawing, only a light tourniquet and a 19 gauge needle were used, and the first 2 mL of blood were discarded. Preparation of the blood samples was designed to avoid the formation of platelet aggregates, using a modified version of the method of Shattil et al., Blood 70:307–315 (1987). Thus, in preparation of whole blood for analysis, there were no washing, centrifugation, gel filtration, vortexing, or stirring steps. Within 15 min. of drawing, whole blood was diluted 1:6 with modified Tyrode's buffer (137 mM NaCl, 2.8 mM KCl, 1 m M MgCl$_2$, 12 mM NaHCO$_3$, 0.4 mM Na$_2$HPO$_4$, 0.35% bovine serum albumin, 10 mM HEPES, 5.5 mM glucose, pH 7.4).

Aliquots of diluted whole blood (15 $\mu$L) were placed in polypropylene tubes containing 2.5 $\mu$L of a saturating concentration of activated platelet-specific biotinylated antibody (either 6D1, FMC25, AK1, PAC1, 10E5, OKM5, or S12) and 2 $\mu$L of 2.5 mM (final concentration) GPRP (Calbiochem, San Diego, Calif.). This method results in an approximately 18-fold dilution of whole blood. Purified human $\alpha$-thrombin (provided by Dr. John W. Fenton II, New York Department of Health, Albany) was added at final concentrations between 0.001 and 10 U/ml. In control assays performed in parallel, buffer only (no thrombin) was added.

The samples were incubated undisturbed (in order to prevent platelet aggregation) for 15 min. at 22° C. A saturating concentration of fluorescein isothiocyanate (FITC)-labeled OKM5 (a platelet-binding antibody which binds to both resting and activated platelets) was added except for those assays containing biotinylated OKM5, in which case a saturating concentration of FITC-labeled AK3 was added. After addition of 3.75 μg phycoerythrin-streptavidin to fluorescently label the activated platelet-specific antibody with the red-fluorescing fluorophore phycoerythrin (Jackson Immuno Research, West Grove, Pa.), the samples were incubated for 15 min. at 22° C. An equal volume of 2% formaldehyde in modified Tyrode's solution was then added and the samples incubated for 30 min. at 22° C. The samples were further diluted approximately three-fold in modified Tyrode's solution and stored at 4° C. before analysis in a flow cytometer. This method of fixation (i.e., fixation after antibody incubations) resulted in no significant differences in fluorescence intensity between samples analyzed immediately and samples analyzed within 24 h.

Sample Analysis

Samples were analyzed in an EPICS Profile flow cytometer (Coulter Cytometry, Hialeah, Fla.), equipped with a 100 mW argon laser and operated at 15 mW power at a wavelength of 488 nm. The fluorescence of FITC and phycoerythrin were detected using 525 nm and 575 nm band pass filters, respectively. Individual platelets were identified by their FITC-positivity (green fluorescence) and their characteristic light scatter; monocytes and any platelet-to-platelet or platelet-to-monocyte aggregates were excluded on the basis of size (light scatter). (Monocytes are the only circulating cells, other than platelets, that bind OKM5.) The binding of the test monoclonal antibody was determined from the phycoerythrin (red) fluorescence. In assays utilizing biotin-OKM5, the platelet-specific antibody used to set a fluorescence threshold was FITC-AK3. Because GPIb is not present on any other circulating blood cell, the thrombin-induced decrease in the binding of AK3 to platelet surface GPIb did not result in fluorescence below the threshold used to distinguish platelets from other cells.

After identification of platelets by FITC-positivity and light scatter gates, binding of biotinylated antibody was determined by analyzing 5,000 or 10,000 individual platelets for phycoerythrin fluorescence. In order to compare results in linear form, data obtained from fluorescence channels in a logarithmic mode were converted to their linear equivalents. Background binding, obtained from parallel assays with purified biotinylated mouse IgM (for PAC1 assays) or IgG (for all other antibody assays) (Calbiochem), was subtracted from each sample. For antibodies 6D1, FMC25, and AK1, the fluorescence intensity of resting platelets was assigned 100 units. For antibodies S12, PAC1, OKM5, and 10E5, the fluorescence intensity of platelets maximally activated with thrombin (10 U/ml) was assigned 100 units.

Thrombin Concentration-dependent Changes in Antibody Binding

Figure 2A:
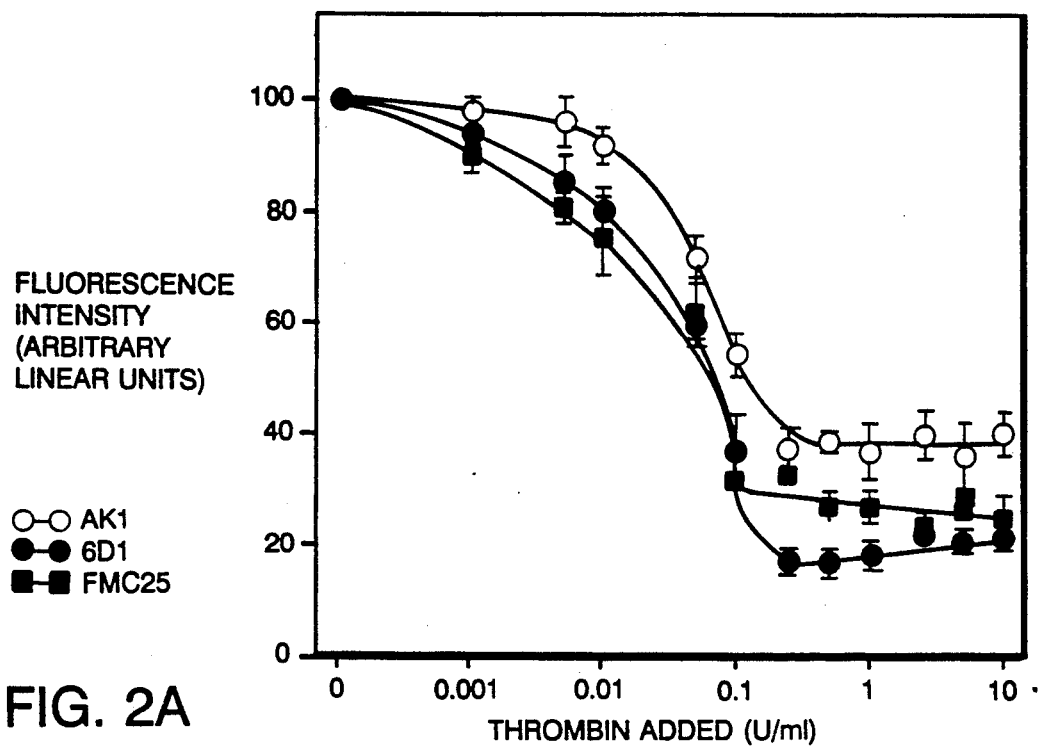
FIG. 2A is a graph showing the effect of thrombin on the binding of monoclonal antibodies to the platelet surface, as determined by flow cytometry of whole blood. For each antibody, the assay was performed as for biotin-S12 in FIG. 1, except for biotin-OKM5, in which case the platelets were identified by FITC-AK3 rather than FITC-OKM5. For each antibody, the fluorescence intensity of resting platelets was assigned 100 units.

Referring to FIG. 2A, thrombin addition resulted in marked reductions in the platelet surface binding of monoclonal antibodies 6D1 (directed against the von Willebrand factor receptor on GPIb), FMC25 (directed against GPIX), and AK1 (directed against the GPIb-IX complex). The maximal thrombin-induced decreases in binding were 79.2±2.1% (6D1), 75.1±4.2% (FMC25), and 60.0±4.2% (AK1) (mean±S.E.M., n=3). Despite these thrombin-induced changes, there was maintenance of the approximately 1:1 ratio of the binding of the GPIb-specific antibody (6D1) and the GPIX-specific antibody (FMC25) at all thrombin concentrations.

Figure 2B:
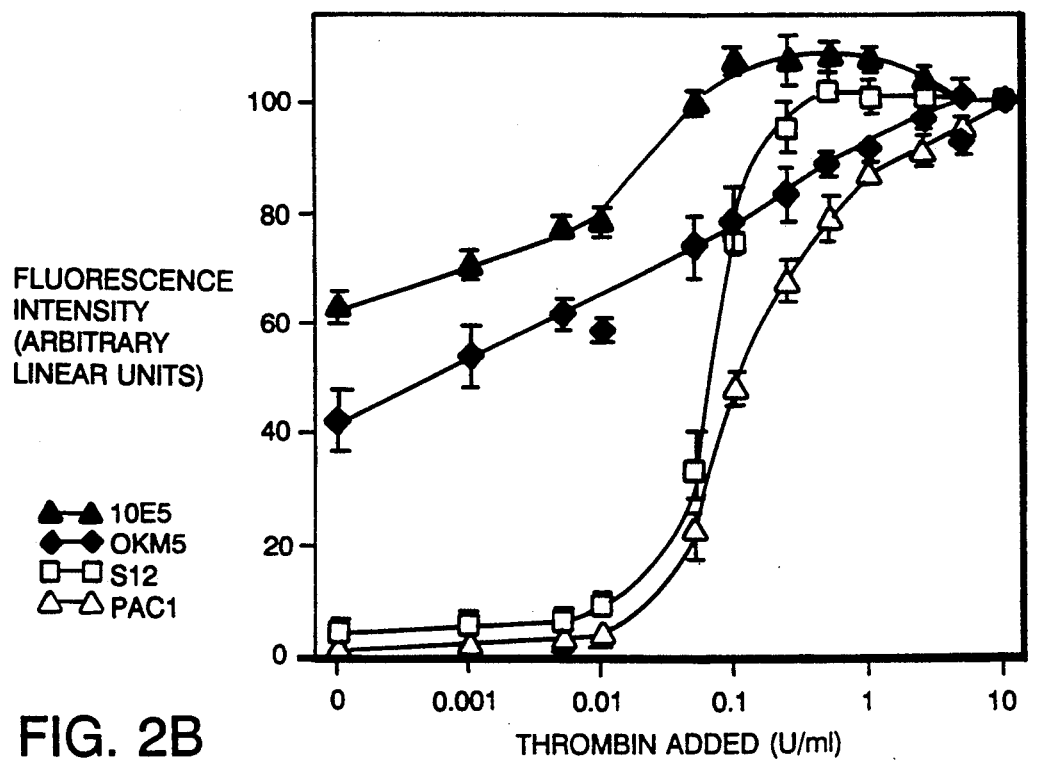
FIG. 2B is a graph showing the effect of thrombin on the binding of monoclonal antibodies to the platelet surface, as determined by flow cytometry of whole blood. For each antibody, the assay was performed as for biotin-S12 in FIG. 1, except for biotin-OKM5, in which case the platelets were identified by FITC-AK3 rather than FITC-OKM5. For each antibody, the fluorescence intensity of maximally activated platelets was assigned 100 units.

Referring to FIG. 2B, in contrast to the findings with the GPIb-IX complex, thrombin resulted in marked increases in the platelet surface binding of monoclonal antibodies S12 (directed against GMP-140), PAC1 (directed against the fibrinogen receptor on the GPIIb-IIIa complex), 10E5 (also directed against the fibrinogen receptor on the GPIIb-IIIa complex), and OKM5 (directed against the thrombospondin receptor on GPIV) (FIG. 2:panel B). The maximal thrombin-induced changes in binding were fold-increases over resting platelets of 28.8±7.1 (S12), 218.4±78.2 (PAC1), 1.6±0.1 (10E5), and 2.5±0.3 (OKM5) (mean±S.E.M., n=3). These increases in fluorescence intensity were not the result of platelet aggregate formation. A lack of binding of antibodies S12 and PAC1 to samples with no added thrombin confirmed that these platelets were in the resting state. In contrast to S12 and PAC1, antibodies OKM5 and 10E5 bound to resting platelets as expected.

Figure 3:
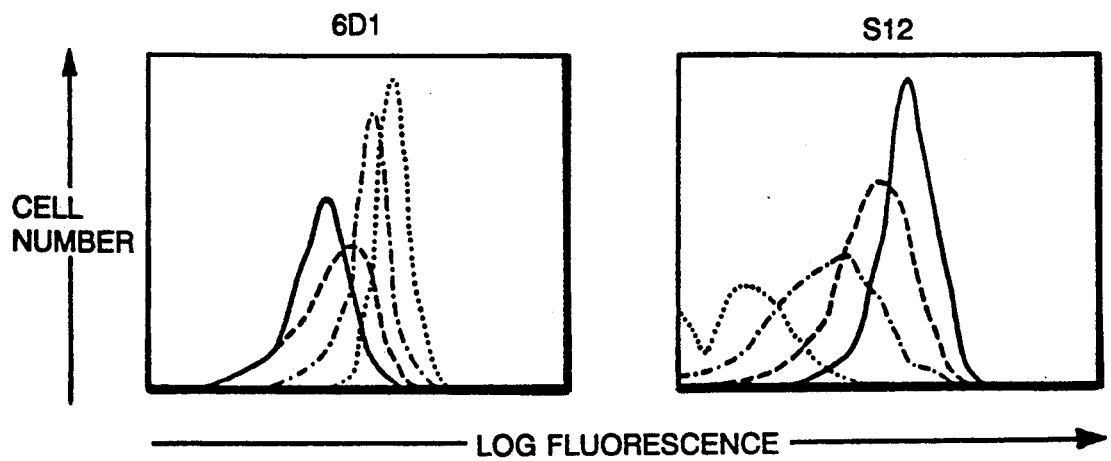
FIG. 3 is a pair of graphs illustrating the effect of thrombin on the binding of monoclonal antibodies to the platelet surface, as determined by flow cytometry of whole blood. Whole blood was activated with thrombin and the binding of antibodies 6D1 and S12 determined as in FIGS. 1 and 2. In the histograms obtained from experiments with 6D1, the final concentrations of thrombin were (from left to right) 1, 0.1, 0.05, and 0 U/ml. In the histograms obtained from experiments with S12, the final concentrations of thrombin were (from left to right) 0, 0.01, 0.05, and 1 U/ml. Each histogram represents data obtained from 10,000 individual platelets. The experiment is representative of three so performed.
Figure 4:
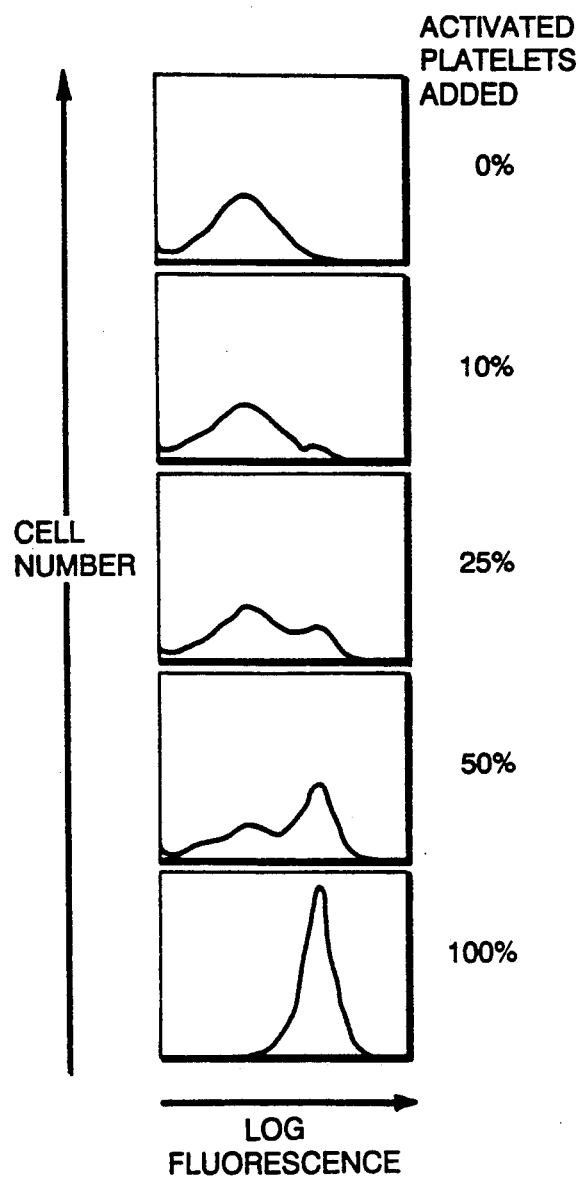
FIG. 4 is a series of graphs of the results of a whole blood mixing study to distinguish maximally thrombin-activated platelets from resting platelets. Aliquots of diluted whole blood were incubated with or without thrombin (10 U/ml) for 15 mins at 22° C., fixed, and then mixed in different proportions. The binding of the activation-dependent antibody S12 was determined as in FIG. 1. The experiment is representative of three so performed.

Because each platelet is analyzed individually, the flow cytometric method of analyzing platelet surface glycoproteins is able to detect distinct subpopulations of platelets. Evidence of thrombin activation was not restricted to a distinct subpopulation of platelets, irrespective of whether there was partial or complete activation of platelets (FIG. 3). A subpopulation of as few as 1% of partially activated platelets could be detected in the whole blood assay (FIG. 4).

Use of Thrombin Activation Test

In numerous pathological or diseased states patients may suffer from abnormalities in platelet reactivity. For example, in coronary artery disease, diabetes, hyperlipoproteinemia, and conditions associated with cigarette smoking or emotional stress patients may be at increased risk of thrombosis from hyperreactive platelets. On the other hand, in some conditions such as congenital bleeding disorders, patients have a hemorrhagic predisposition from hyporeactive platelets. Use of the platelet reactivity whole blood assay to determine the extent of abnormal platelet reactivity in an individual patient permits individual risk assessment and makes possible early administration of intervention therapies.

Preparation of Whole Blood Samples from Bleeding Time Wounds for Flow Cytometric Analysis A modified version of the method of Abrams et al. (Blood 75:128, 1990) was used. A standardized bleeding time test was performed on normal adult volunteers who were not cigarette smokers and who had not ingested aspirin or other drugs within the previous 10 days. With the subject seated, a sphygmomanometer cuff was applied to the upper arm at a pressure of 40 mM Hg and a horizontal incision was made on the volar aspect of the forearm using a Simplate-I (Organon Teknika Corp., Jessup, Md.). The blood emerging from the bleeding time wound was collected with a micropipet at 1 min. intervals until the bleeding stopped. After each pipetting, any residual blood at the bleeding time wound site was removed with a filter paper. The wound was not touched by the pipet tip or the filter paper. The pipetted blood (2 μL per antibody tested) was added to a microfuge tube containing acid-citrate-dextrose, immediately fixed by incubation (30 min, 22° C.) with an equal volume of 2% formaldehyde, and diluted 1:6 by volume in modified Tyrode's buffer. The samples were then incubated (15 min, 22° C., in the dark) with saturating concentrations of a FITC-labeled monoclonal antibody (OKM5 or AK3) and a biotinylated monoclonal antibody (AK1, FMC25, 6D1, AK3, S12, or OKM5). In control assays, biotinylated mouse IgG was used. The samples were then incubated (15 min, 22° C., in the dark) with phycoerythrin-streptavidin and further diluted approximately three-fold in modified Tyrode's buffer, before storage at 4° C. prior to flow cytometric analysis. Control assays were performed with peripheral blood drawn from the antecubital vein of the opposite arm of the same subject through a 21-gauge butterfly needle and tubing just before the bleeding time. After discarding the first 2 mL, one drop of nonanticoagulated blood from the butterfly tubing was placed on a piece of parafilm and aliquots were processed for flow cytometry exactly as described for the bleeding time samples. That the platelets in these control samples were in a resting state was demonstrated by the lack of S12 binding (<5% of the S12 binding of samples activated with thrombin 10 U/mL).

Flow cytometric analysis of whole blood was then performed as described above. Specifically, platelets were identified in whole blood by the binding of an FITC-labeled monoclonal antibody to GPIV and monocytes were gated out by size (light scatter). This novel technique enabled us to quantitate activation-dependent changes in platelet surface GPIb by analysis of the binding of biotinylated anti-GPIb monoclonal antibodies.

The above-described method provides a means of determining in vivo activation-dependent changes in GPIb in response to the most physiological stimulus: a wound. Comparison to normals will identify patients with hyperreactive or hyporeactive platelets predisposing to thrombosis and hemorrhage, respectively.

The standarized bleeding time is in widespread clinical use as test of primary hemostasis. The above-described method is an extension of the bleeding time method that requires no further blood from the patient (because blood that would normally be discarded is used).

Other Embodiments

Other embodiments are within the following claims. For example, any analogue of GPRP that prevents the polymerization of fibrin monomers can be used to block fibrin clot formation in the whole blood assay. Other methods of detecting thrombin-activated platelets could be employed in addition to flow cytometry such as radio-immunoassay methods. In the flow cytometry method, platelets can also be detected by their light scattering properties, prior to the thrombin activation step; further, monoclonal antibodies against other platelet surface receptors, or additional monoclonal antibodies known to react with the receptors described above, can be employed to detect either all platelets or activated platelets. Although human α-thrombin is preferred, any thrombin can be used, e.g., gamma and beta thrombin, and other mammalian thrombins, e.g., bovine thrombin.

What is claimed is:

1. A method of determining thrombin reactivity of platelets in a whole blood sample comprising
   adding to the whole blood sample a first antibody which is specific for an α-thrombin activated surface antigen of the platelets, and an agent which binds to fibrinogen and fibrin monomer to inhibit α-thrombin induced fibrin polymerization,
   allowing the agent to bind to the fibrinogen and fibrin monomer,
   adding α-thrombin to the whole blood sample to activate a surface antigen of the platelets, wherein the first antibody binds to the activated surface antigen of the platelets,
   binding to the platelets a second antibody specific for another surface antigen of the platelets, and
   detecting the amount of the first and second antibodies bound to the platelets.

2. The method of claim 1, wherein the first and second antibodies are labeled antibodies.

3. The method of claim 2, wherein the labels are fluorescence emitting labels.

4. The method of claim 3, wherein the fluorescence emitting labels of the first and second antibodies emit at different wavelengths.

5. The method of claim 1, wherein the antibodies are detected by flow cytometry.

6. The method of claim 1, wherein the surface antigen which binds the second antibody is other than GPIb.

7. The method of claim 6, wherein the surface antigen which binds the second antibody is GPIV.

8. The method of claim 1, wherein the surface antigen which binds the first antibody is selected from the group consisting of GPIb, GPIX, GPIIb-IIIa complex, and GMP-140, and the surface antigen which binds the second antibody is GPIV.

9. The method of claim 8, wherein the surface antigen which binds the first antibody is GPIV and the surface antigen which binds the second antibody is GPIb.

10. The method of claim 1 wherein said agent competitively inhibits fibrin monomer polymerization.

11. The method of claim 10 wherein said agent is capable of binding to a fibrinogen molecule to inhibit the binding of said molecule to other fibrinogen molecules.

12. The method of claim 11 wherein said agent mimics, in its fibrinogen binding property, the action of the amino-terminal half of native human fibrinogen.

13. The method of claim 12 wherein said agent comprises a peptide.

14. The method of claim 5 wherein said peptide contains between four and twenty amino acid residues.

15. The method of claim 14 wherein said peptide contains between 4 and 10 amino acid residues.

16. The method of claim 13 wherein said peptide has at least 75% homology with a region contained in the amino-terminal half of native human fibrinogen.

17. The method of claim 16 wherein said peptide comprises the tetrapeptide glycyl-L-prolyl-L-arginyl-L-proline.

18. The method of claim 1 wherein said agent comprises an antibody capable of binding to the amino-terminal half of native human fibrinogen.

* * * * *

UNITED STATES PATENT AND TRADEMARK OFFICE
CERTIFICATE OF CORRECTION

PATENT NO. : 5,246,832
DATED : September 21, 1993
INVENTOR(S) : Alan D. Michelson, et al It is certified that error appears in the above-indentified patent and that said Letters Patent is hereby corrected as shown below:

On title page, item [56] under "PUBLICATIONS",
column 2, line 4, "Demonstrate" should be --Demonstrated--;

On title page, item [56] "PUBLICATIONS", page 2, line 1, "Carbalho" should read --Carvalho--

Column 2, line 34, after "wherein", insert the following:

--Fig. 1 is a set of graphs showing flow cytometric analysis of platelets in whole blood. (Refer to the Table, *infra*, for antibody antigens.) Diluted whole blood in the presence of 2.5 mM GPRP, a saturating concentration of FITC-OKM5, and a saturating concentration of biotin-S12, was--

Signed and Sealed this

Twelfth Day of April, 1994

*Attest:*

BRUCE LEHMAN

*Attesting Officer*  *Commissioner of Patents and Trademarks*